US00PP18318P2

(12) United States Plant Patent
Bergeron

(10) Patent No.: US PP18,318 P2
(45) Date of Patent: Dec. 18, 2007

(54) ***HOSTA* PLANT NAMED 'PINEAPPLE PUNCH'**

(50) Latin Name: ***Hosta* sp. (*Tratt.*)**
Varietal Denomination: Pineapple Punch

(75) Inventor: Amy Bergeron, Holland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 11/442,941

(22) Filed: May 30, 2006

(51) Int. Cl.
*A01H 5/00* (2006.01)

(52) U.S. Cl. ..... Plt./353
(58) Field of Classification Search ..... Plt./353
See application file for complete search history.

*Primary Examiner*—Kent Bell
*Assistant Examiner*—Annette H Para

(57) ABSTRACT

A new and distinct *Hosta* plant named 'Pineapple Punch', characterized by narrow pointed leaves having creamy yellow margins, and a deep green center, that displays a arching habit, and light lavender flowers held above the foliage on thick gray-green scapes.

2 Drawing Sheets

Botanical classification: *Hosta* sp. (Tratt.).
Variety denomination: 'Pineapple Punch'.

BACKGROUND OF THE INVENTION

The present invention relates to the new and distinct cultivar of *Hosta,* botanically known as *Hosta* hybrid (Tratt.), and hereinafter referred to as the cultivar 'Pineapple Punch'.

The new plant was discovered by the inventor, Amy Bergeron as a non-induced, naturally occurring whole plant mutation of *Hosta* 'Pineapple Upsidedown Cake' (not patented) in a greenhouse at a nursery in Zeeland, Mich., USA. Asexual propagation of the plant as the same nursery by tissue culture and division has shown that the unique and distinct characteristics of this new plant are stable and reproduce true to type in successive generations.

SUMMARY OF THE INVENTION

*Hosta* 'Pineapple Punch' is unique from its parent sport, *Hosta* 'Pineapple Upsidedown Cake' (not patented) and all other *hosta* cultivars known to the inventor, in several traits. *Hosta* 'Pineapple Upsidedown Cake' is a sport of *Hosta* 'Pineapple Poll' (not patented), a hybrid of *H. lancifolia*×*H. sieboldiana* made by Eric Smith. *Hosta* 'Pineapple Poll' is a solid green-leafed *hosta* with long pointed leaves, heavy substance and a coarse wave or piecrust-like edge. 'Pineapple Upsidedown Cake' is the same leaf form, smaller in size, with a light yellow to cream center and dark green margin. 'Pineapple Punch' is a reverse-pattern variegation of 'Pineapple Upsidedown Cake' with the light yellow to cream color on the leaf margin and dark green center. All three plants have similar growth and flowering habits except that 'Pineapple Upsidedown Cake' is a slower grower and smaller mature size.

BRIEF DESCRIPTION OF THE DRAWINGS

The photographs of the new plant demonstrate the overall appearance of the plant including the unique traits. The colors are as accurate as reasonably possible with color reproductions. Some slight variation of color may occur as a result of lighting quality, intensity, wavelength, direction or reflection.

FIG. 3 shows the bottom side of the leaf.

DETAILED BOTANICAL DESCRIPTION

Figure 1:
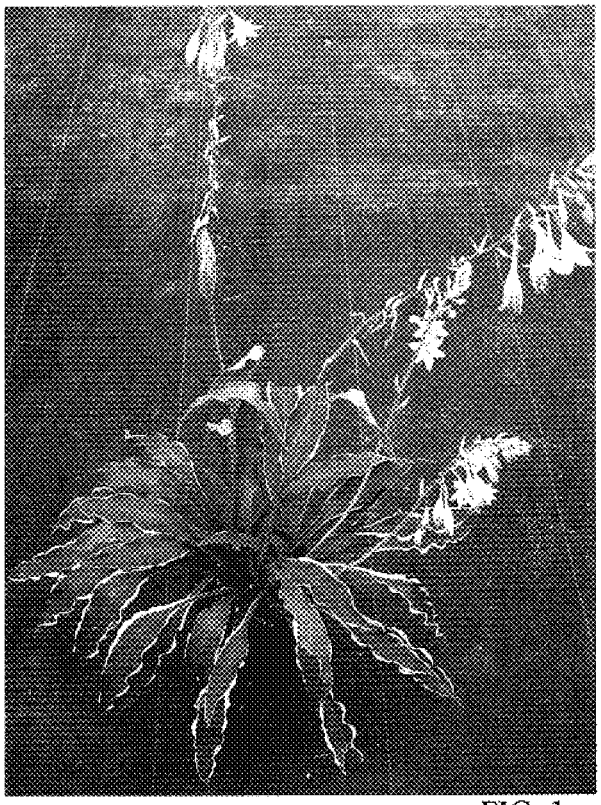
FIG. 1 shows the plant with scapes, flowers and buds.
Figure 2:
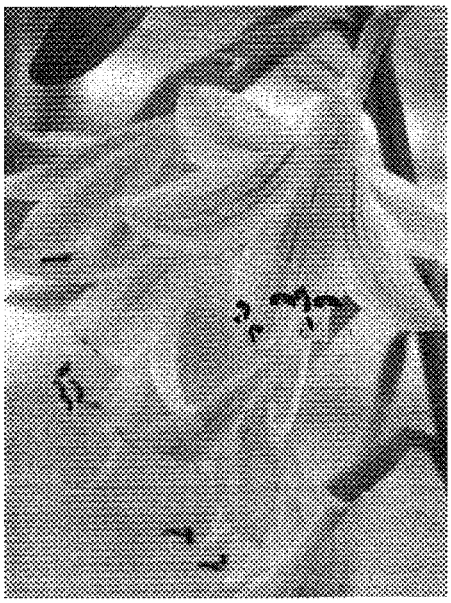
FIG. 2 shows a close up of the flowers.
Figure 3:
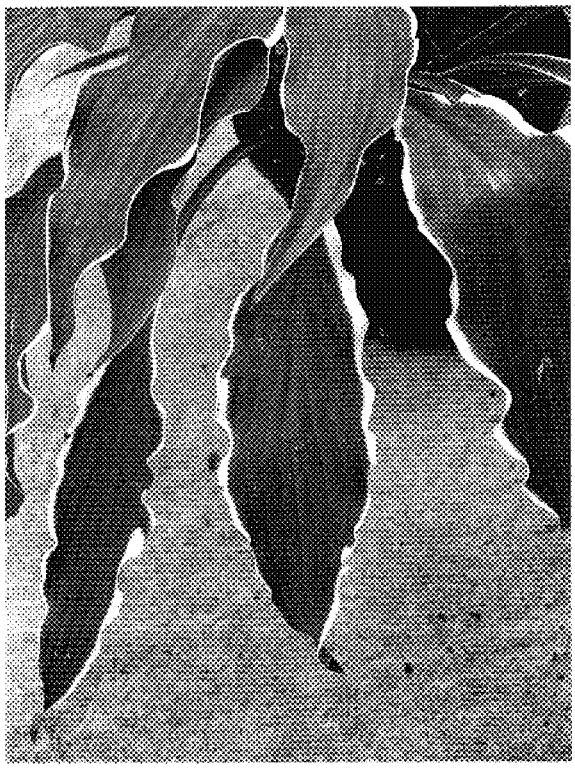
FIG. 3 shows the top side of a leaf with the intricate leaf colors.
Figure 4:
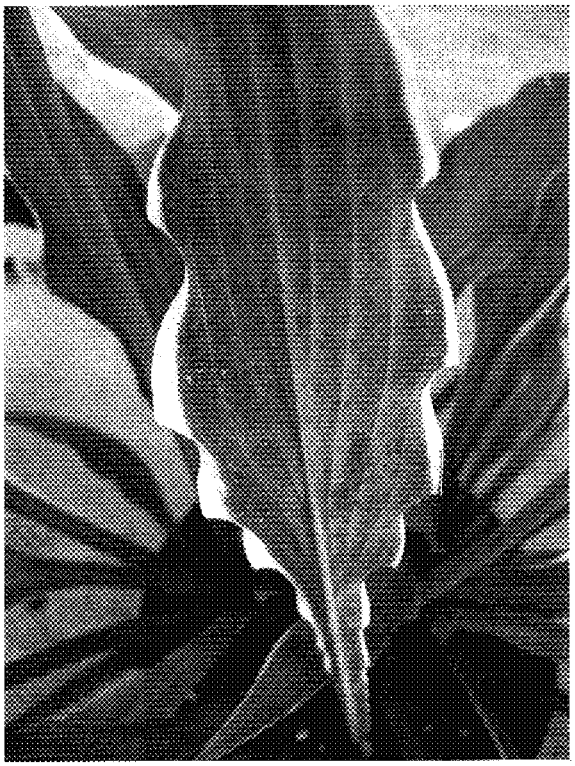

The following descriptions and color references are based on The Royal Horticultural Society Colour Chart (2001 edition) except where common dictionary terms are used. The new plant, *Hosta* 'Pineapple Punch', has not been observed under all possible environments. The phenotype may vary slightly with different environmental conditions, such as temperature, light, fertility and moisture, but without any change in the genotype. The following observations and size descriptions are of a three-year old plant in a one gallon container grown in Zeeland, Mich., USA under 50% supplemental shade, day temperatures of 18 to 32 degrees C., and night temperatures of 14 to 22 degrees C.

Botanical classification: *Hosta* sp. cultivar 'Pineapple Punch'.

Parentage: Naturally occurring whole plant mutation of *Hosta* 'Pineapple Upsidedown Cake' (not patented).

Propagation: Method by tissue culture and division, Time to initiate roots from both division and tissue culture about three weeks.

Rooting habit: Normal, fleshy, to 3 mm thick, lightly branching.

Plant habit: Herbaceous, moderately loose rhizomatous perennial, symmetrical, radical glabrous above and glaucous underneath leaves upright and erect through flowering period, (14 to 16 leaves per division), more horizontal late in the season and in maturity.

*Crop time.*—Under normal summer greenhouse growing conditions about 16 weeks to finish in a one-liter container. Plant vigor is very good.

*Plant size.*—Foliage at flowering is 30 to 35 cm tall and 40 to 50 cm wide.

Foliage description:

*Shape and size.*—Ovate to broadly ovate leaf blades have an acute apex and cordate base. The leaf blades are 18 to 20 cm long and 5 to 7 cm wide. The leaf blade margin is entire and the cream to light yellow variegation pattern on the edge varies in different regions of the leaf from 3 to 6 mm wide. Petioles are 14 to 16 cm long and 5 mm wide in the center broadening slightly at the plant base (ground) and tapering at the leaf blade.

*Venation.*—Parallel, same color as surrounding leaf surface on the top and slightly whiter on the bottom.

*Leaf blade color.*—Adaxial (upper) surface: early season a deep green closest to RHS 137 C in the center, RHS 154 D on the margin. Later in the growing season the center is greener than RHS 127 A and bluer than RHS N138 A; the margin lightens to RHS 11 D. Abaxial (lower) surface: early in the season is RHS N 138 D on the center and RHS 144 C on the margin. Later in the season the lower surface is RHS N 138 C in the center and RHS 11 D on the margin.

There is no clear intermediate color band on either surface, but rather a melded yellow-green RHS 154 B on older leaves with an occasional green line the same color as the top or bottom center protruding into the margin.

Petioles colors are the same as the respective leaf colors with the margins being more greenish-yellow in the shadier portions and more creamy-colored in higher light levels. The basal one third of the petiole has a gradient of reddish purple stipling RHS 61 A increasing in quantity (density) closer to the ground.

Flower description:

*Buds.*—Torpedo-shaped, flared at apex; two days prior to opening the buds are between RHS 75 C and RHS 75 D with veins of RHS 70 B; and RHS 85 A, 6 to 7 cm long, up to 1.5 cm wide.

*Peduncle.*—7 to 9 mm in diameter, erect to 95 cm; closest to RHS N 138 C with some RHS 61 A stipling near base.

*Pedicel.*—1 to 1.2 cm long, 3 mm in diameter, curved slightly downward, RHS N 80 D.

*Flowers.*—30 to 36 per scape, 4 to 6 scapes per plant; funnelform; 5 to 7 cm wide and 6 to 8 cm long, (distal flowers being smaller) subtended by a simple, entire, narrowly-acute, sessile bract with base wrapped around scape, up to 2 cm long and 7 to 10 mm wide with a border on both surfaces lighter than RHS 59 D and center on both surfaces closest to RHS 143 D; flowers persist for a normal period, up to two days on or off the plant, and the scapes remain effective from early to late August. No fragrance has been detected.

*Tepal.*—Six, simple, entire, fused at the base, oblong to elliptic, with slightly-recurved acute apex, approximately 5 to 6 cm long and 1.5 cm wide, arranged in two layers of three, the inner three with clear 1 to 2 mm margin toward the apex, main adaxial (inner) color in center of tepals is Red purple RHS 25 B and three prominent violet stripes of RHS 84 B. The back of the tepals is between RHS 76 B and 76 C with less obvious stripes about RHS 71 C.

*Gynoecium.*—Single, style — 7 to 8 cm long, 2 mm diameter, near white, curled upward at distal end; Stigma — entire, white, up to 3 mm diameter.

*Androecium.*—Filaments — six, white, approximately 1 mm in diameter and up to 5 cm long; curved at tips.

*Anthers.*—5 to 6 mm long, 2 mm wide, about RHS N 79 A around margin of abaxial side, white in center, pollen is yellow-orange RHS 17 B.

Fruit: Tri-valve, longitudinally dehiscent capsule, about 2.5 to 3 cm long and 5 mm diameter, when mature is a combination of RHS 164C, RHS 165B and some regions of RHS N167 B; as developing RHS.

Seeds: flat winged samara with embryo at one end, 10 to 24 per pod, approximately 10 mm long and 3 mm wide.

Disease resistance: The plant grows best with plenty of moisture but is able to tolerate some drought especially once established. Hardiness to at least USDA zone 3, and other disease resistance is typical of other *hostas*.

I claim:

1. A new and distinct cultivar of ornamental *Hosta* plant named 'Pineapple Punch' as herein described and illustrated, suitable as a potted plant, for landscaping specimen or in mass, and for fresh-cut arrangements.

* * * * *